United States Patent [19]

Hofmann et al.

[11] Patent Number: 5,688,233

[45] Date of Patent: *Nov. 18, 1997

[54] ELECTRONINCORPORATION ENHANCED TRANSDERMAL DELIVERY OF MOLECULES

[75] Inventors: Gunter A. Hofmann; Lei Zhang, both of San Diego, Calif.

[73] Assignee: Genetronics, Inc., San Diego, Calif.

[*] Notice: The term of this patent shall not extend beyond the expiration date of Pat. No. 5,464,386.

[21] Appl. No.: 552,200

[22] Filed: Nov. 2, 1995

Related U.S. Application Data

[63] Continuation-in-part of Ser. No. 310,647, Sep. 22, 1994, Pat. No. 5,464,386, which is a continuation-in-part of Ser. No. 219,970, Mar. 30, 1994, Pat. No. 5,462,520, which is a continuation-in-part of Ser. No. 931,061, Aug. 17, 1992, Pat. No. 5,318,514.

[51] Int. Cl.$^6$ .................... A61N 1/30; A61K 38/00
[52] U.S. Cl. .................... 604/20; 607/145; 607/150
[58] Field of Search .................... 604/19, 20; 607/149, 607/150, 153; 428/402; 424/448, 449, 450

[56] References Cited

U.S. PATENT DOCUMENTS

| | | | |
|---|---|---|---|
| 4,921,757 | 5/1990 | Wheatley et al. | 428/402.2 |
| 4,955,378 | 9/1990 | Grasso | 128/421 |
| 5,002,527 | 3/1991 | Reller et al. | 604/20 |
| 5,019,034 | 5/1991 | Weaver et al. | 604/20 |
| 5,098,843 | 3/1992 | Calvin | 435/287 |
| 5,137,817 | 8/1992 | Busta et al. | 435/173 |
| 5,149,539 | 9/1992 | Ledger et al. | 424/449 |
| 5,160,741 | 11/1992 | Cormier et al. | 424/450 |
| 5,162,043 | 11/1992 | Lew et al. | 604/20 |
| 5,236,413 | 8/1993 | Feiring | 604/21 |
| 5,312,325 | 5/1994 | Sibalis | 604/20 |

*Primary Examiner*—Jennifer Bahr
*Assistant Examiner*—Stephen Huang
*Attorney, Agent, or Firm*—Baker, Maxham, Jester & Meador

[57] ABSTRACT

A method of transdermal molecular delivery comprising molecules to be delivered mixed with particles, contacting a selected area of a skin surface with the particles and molecules, applying a pulsed electric field of sufficient amplitude and duration to induce dielectric breakdown of the stratum corneum, and applying a pressure to the molecules to force transport of the molecules through the pores in the stratum corneum into the underlying skin.

28 Claims, 3 Drawing Sheets

ELECTRONINCORPORATION ENHANCED TRANSDERMAL DELIVERY OF MOLECULES

REFERENCE TO RELATED APPLICATION

The present application is a continuation-in-part of application Ser. No. 08/310,647, entitled "TRANSDERMAL DRUG DELIVERY BY ELECTROINCORPORATION OF VESICLES", filed Sep. 22, 1994, now U.S. Pat. No. 5,464, 386, which is a continuation-in-part of application Ser. No. 08/219,970, entitled "TRANSSURFACE DRUG DELIVERY BY ELECTROFUSION OF MICROBUBBLES TO THE TISSUE SURFACE", filed Mar. 30, 1994, now U.S. Pat. No. 5,462,520, which is a continuation-in-part of application Ser. No. 07/931,061, entitled "APPLICATOR FOR THE ELECTROPORATION OF DRUGS AND GENES INTO SURFACE CELLS", filed Aug. 17, 1992 now U.S. Pat. No. 5,318,514 dated Jun. 7, 1994.

BACKGROUND OF THE INVENTION

The present invention relates to drug delivery and pertains particularly to a method and apparatus for the transdermal delivery and extraction of drugs and other molecules.

The medical community has long sought improved methods of transdermal delivery of medications, drugs and other molecules and fluids without physical invasion of the tissue surface.

In the aforementioned applications, there is disclosed an apparatus and method for the electroporation of drugs, immunizing agents, and genes into surface cells, and a method and apparatus for the transdermal drug delivery by electroincorporation of vesicles into the tissue surface. In another co-pending application Ser. No. 07/907,322, entitled ELECTROPORATION METHOD AND APPARATUS FOR INSERTION OF DRUGS AND GENES INTO ENDOTHELIAL CELLS, filed Jul. 1, 1992, now U.S. Pat. No. 5,304,120 certain methods and apparatus are disclosed for insertion of drugs and genes into endothelial cells. The teachings of these are incorporated herein by reference.

In the second aforementioned parent application, there are disclosed methods and apparatus for the electroporation of drugs, immunizing agents, and genes into surface cells. In that application, apparatus is disclosed for delivery of a fluid medium carrying preselected molecules to a tissue surface and thereafter applying electrical signals by means of electrodes to the surface tissue. The field is applied at a predetermined strength and duration in order to make the walls of the tissue surface transiently permeable to permit the molecules to pass through the tissue surface into underlying tissue. Further electroporation can enable the molecules to enter preselected cells without damaging them.

One difficulty with the prior apparatus is that the stratum corneum (SC) which consists of a thin layer of dead cells with a high electrical resistance presents a major obstacle to the administration of drugs and genes transdermally. This layer can be perforated by the administration of short electrical field pulses, which creates a dielectric breakdown of the stratum corneum forming pores which can allow the passage of molecules. However, in order to transport solutions containing molecules through the pores, a driving force is needed. In some applications this driving force can be provided by iontophoresis. However there are many situations in which iontophoresis cannot be used or may not be suitable.

Among the prior art relating generally to this field is the Weaver et al patent U.S. Pat. No. 5,019,034 entitled "Control of Transport of Molecules Across Tissue Using Electroporation". Weaver seeks an alternative to the traditional syringe and gun injection of medications. He describes a proposal for using high voltage, short duration electrical pulses on the skin surface to produce electroporation of the tissue to enable drugs and medication to pass into the tissue. However, he does not recognize or address the problem of the obstacle provided by the stratum corneum.

The co-pending parent application presents an invention designed to overcome the problems of the prior art by providing means to overcome the resistance to the administration of drugs transdermally presented by the stratum corneum. In accordance with that invention, drugs, immunizing agents, or genes are loaded into vesicles, the vesicles are brought into physical contact with the skin surface and a pulsed electrical field is applied between the vesicles and the tissue by means of electrodes. This forms pores at the interface of the vesicles and the skin, such that the vesicles are pulled through a channel by dielectrophoretic force.

While that approach is shown to be successful to transport effective amounts of molecules of drugs and the like in or into the skin, it requires encapsulation into vesicles. It is desirable to transport drugs or the like in solution in or into the skin.

SUMMARY AND OBJECTS OF THE INVENTION

It is the primary object of the present invention to provide an improved method and apparatus for transdermal drug delivery by electroporation.

In accordance with the primary aspect of the present invention, drugs or genes are brought into physical contact with the skin surface, an electrode is contacted with the surface and a pulsed electrical field is applied to the skin surface by means of electrodes. This forms pores in the stratum corneum (SC), and pressure is applied to the skin surface forcing drugs or genes or immunizing agent through the SC into the skin.

Another aspect of the invention utilizes particles which may be inert, biodegradable, or depot microspheres containing drugs, to increase the efficiency of delivery by creating or enlarging channels through which the drugs or genes or immunizing agents under pressure can penetrate in increased amounts.

A further aspect of the invention includes a vacuum to draw fluid from the tissue following electroporation.

BRIEF DESCRIPTION OF THE DRAWINGS

The above and other objects and advantages of the present invention will be appreciated from the following specification when read in conjunction with the accompanying drawings wherein.

DETAILED DESCRIPTION OF THE PREFERRED EMBODIMENTS

Figure 1:
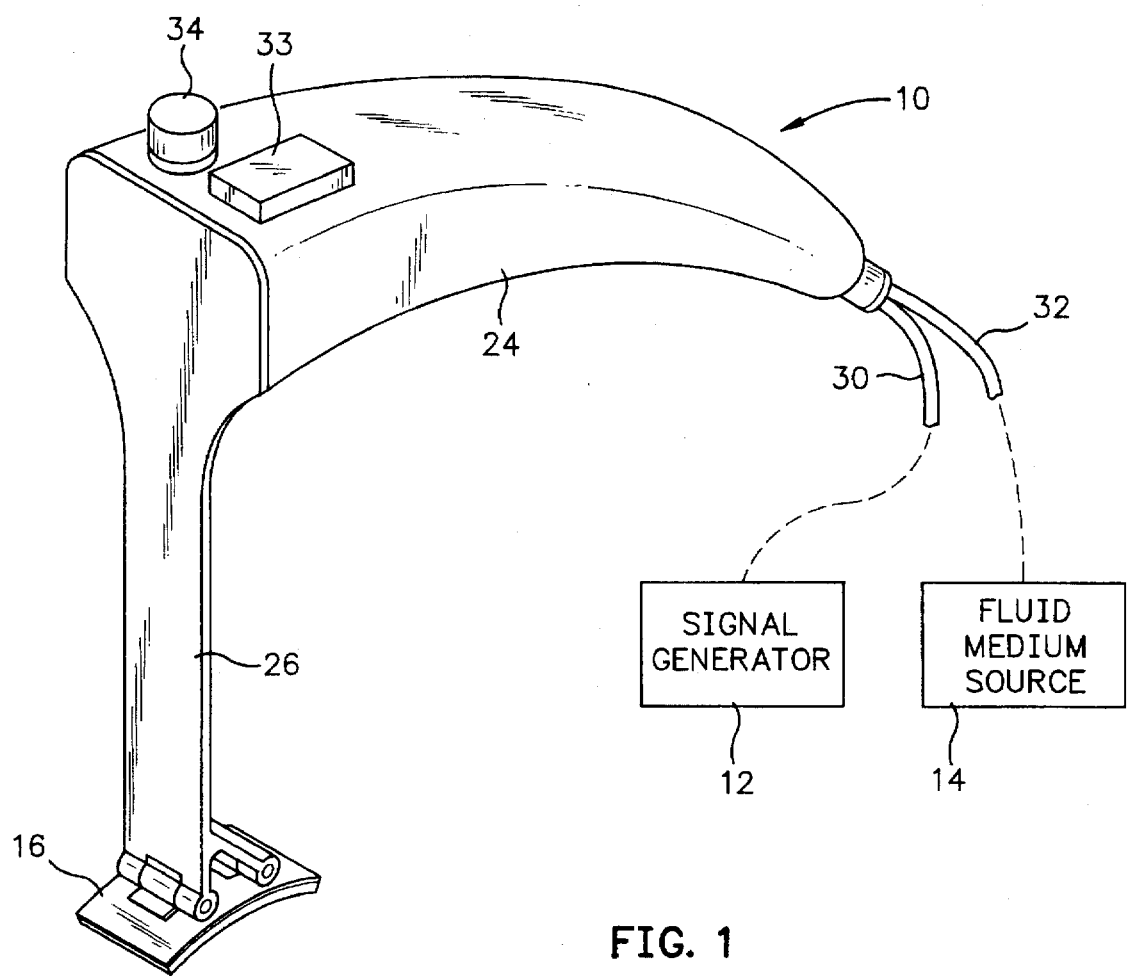
FIG. 1 is a perspective view of an apparatus for carrying out the process of the present invention.

The present invention was devised to overcome the problem presented by the stratum corneum. However, it is applicable to the extraction of fluids and/or insertion of molecules such as drugs and genes across other tissue surfaces in body cavities and open wounds. Certain modifications may be necessary to the various illustrated and described apparatus for these and other applications.

The present invention takes advantage of dielectric breakdown of the stratum corneum (SC) to transfer molecules and/or vesicles containing molecules such as drugs and genes across the SC surface into the underlying tissue and possibly into the blood stream. A force or pressure is preferably applied to the molecules to increase the rate of transport through the SC or tissue. When desirable, subsequent electroporation may be applied to improve the uptake of drugs, genes, DNA or the like, into cells in the living tissue of humans and other living organism. The present invention may also be used to withdraw fluids and or certain molecules from tissue or the blood stream by the application of vacuum or a negative pressure.

Electroporation involves the transient formation of pores in tissue or cell membranes utilizing one or more short pulses of high-voltage electric field. Once these pores are formed in the tissue, fluids containing drugs, DNA and other molecules can pass into and through the tissue. Once in the tissue, pores in cell membranes, enable DNA and other molecules to enter the cells through these pores in the cell walls. Thereafter, they stay encapsulated in the cell and the cell walls reseal themselves. The DNA or other gene or drug can then act within the cell to alter the cell properties. Fluids can also be more easily withdrawn from the tissue with electroporation.

It is known that iontophoresis can be used as a driving force to force molecules across tissue surfaces. We have found that various other techniques can be used to apply a driving force or pressure to the fluid or molecules to force them through surface and other tissue. We have also found that this force or pressure may be applied during the application of electrical pulses or up to one minute after the application of the electrical pulses. Transdermal resistance measurements has shown that the skin remains in a low resistance state for up to one minute after the application of electrical pulses. Thus, the fluid can also be applied to the tissue surface up to one minute after the application of the electrical pulses.

The present invention can be used to enhance the introduction of molecules across skin surfaces. When dealing with the Stratum Corneum (SC) the flux can be increased for a given pressure, if the pores are increased by electroincorporation of particles simultaneously with the solution. These particles whose functions are to punch larger holes in the SC can be inert particles such as gold particles, or biodegradable particles. The particles could also be filled with the molecules to be delivered as more fully disclosed in U.S. Pat. No. 5,464,386 which is incorporated herein by reference. As disclosed in that application various techniques including electroporation is used to load molecules such as drugs and DNA into vesicles of a size up to several µm diameters. The vesicles are then applied to the SC and electrodes are then applied over the vesicles. Electrical field pulses are then used to create dielectric breakdown of the stratum corneum or other tissue surface forming passages through which the vesicles and the drugs or other molecules pass into the underlying tissue. The vesicles are then broken down and the molecules diffused into the tissue. Pressure can be applied by the weight of the electrode or by simple manual pressure on the electrode.

Figure 2:
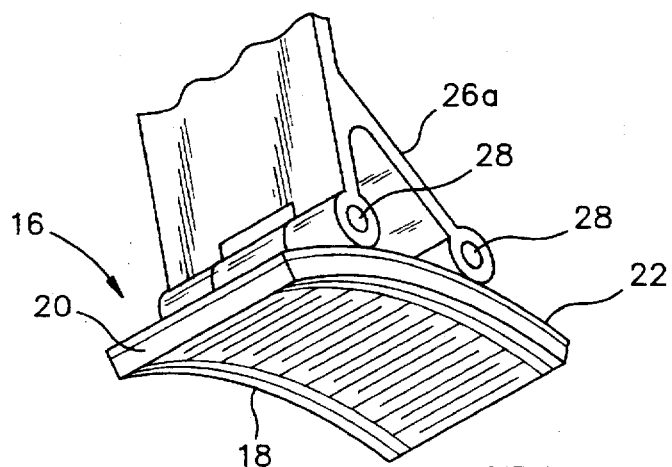
FIG. 2 is an enlarged view of the head assembly of the FIG. 1 embodiment.

Referring to FIG. 1, an exemplary embodiment of an apparatus which may be utilized in carrying out the process of the present invention, is illustrated. The device comprises a manually positionable applicator designated generally by the numeral 10 which is connected to a signal generator 12 and a pressurized fluid medium source 14 which preferably includes a pump. The applicator 10 has a head assembly 16 which engages and applies a fluid containing molecules of genes, immunizing agents or drugs and vesicles; and electrical pulses to a preselected surface tissue region of a patient. Further details of the head assembly are illustrated in FIG. 2.

The head assembly comprises an electrode array 18 which is carried or mounted on a carrier or applicator such as an open pore foam elastomer 20 carried by flexible semirigid or firm dielectric planar support member 22. Adjacent parallel segments of conductors serve as opposed electrodes for application of the electric field to the tissue surface. The electrodes are preferably small and closely spaced, such as about 0.2 mm width at about 0.2 mm spacing. The applicator may also be a small patch with electrodes on a surface thereof.

The applicator 10 (FIG. 1) further includes a handle portion 24 and an arm portion 26 on which is mounted the head assembly 16. The head assembly 16 is connected to a Y-shaped distal end 26a by means of a pair of pins 28. These pins enable the head to flex and conform to the curvature of the skin surface.

The terminal ends of the conductors or electrodes of array 18 are connected to the signal generator 12 by way of an electrical cable 30. A fluid medium carrying the molecules or drugs and vesicles is supplied from the fluid medium source 14, which may include a suitable motorized pump or pressure source, not shown. The fluid medium source 14 is coupled to the elastomer foam 20 by flexible tube 32 which extends to the applicator 10 and to the foam applicator. An actuator button 30 on the handle 24 of the applicator may be depressed to activate a valve (not shown) and deliver a suitable quantity of the fluid medium to the foam elastomer 20. The elastomer 20 provides a sponge-like substrate for holding a predetermined quantity of the fluid medium. The applicator and signal generator functions as more fully described in the aforementioned parent application, now allowed, which is incorporated herein by reference as though it were fully set forth. With this applicator a driving pressure may be applied by the fluid pressure of the fluid, or simply by manual manipulation of the applicator by pressing it against the tissue surface.

Figure 3:
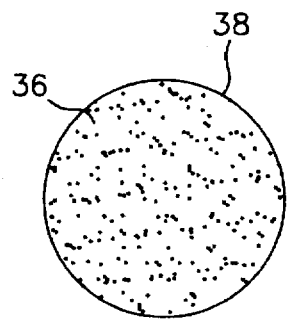
FIG. 3 is a diagrammatic illustration of a vesicle loaded with molecules of drugs, immunizing agents or genes.

Referring to FIG. 3, a particle 38 is illustrated which may be used by electroincorporation simultaneously with the solution to increase the pore size and flux. These particles used to punch holes in the SC can be inert particles such as gold, or biodegradable particles. They can also be filled with the molecules 36 to be delivered if an extended time release profile is desired. These particles may be vesicles such as liposomes, erythrocyte ghosts or other vesicles. The vesicles may also be of a matrix design where the drug or other molecules are encapsulated within the matrix. This would enable the provision of a time release function. The encapsulation of the molecules can be carried out by any one of a number of known processes, including electroporation.

The loaded vesicles are then brought into contact with the tissue surface or stratum corneum of a skin layer by suitable means and are positioned between pairs of closely spaced electrodes. This can be carried out by the apparatus of FIG. 1, wherein a fluid carry the vesicles and applied by the sponge 20 would be positioned between the electrodes 18 on the surface of the applicator.

Thereafter, a short voltage pulse is applied between the electrodes so that the electric fields of sufficient amplitude are generated to induce dielectric breakdown forming pores in the stratum corneum. A suitable force is then applied to the solution containing the vesicles to force the vesicle to pass through the pores into the underlying tissues. The electric field is applied so that useful electric field lines are perpendicular to the tissue surface or stratum corneum surface. Typical electrical parameters for the stratum corneum are a field strength of 20 to about 60 kV/cm, which can be generatored with moderate voltages of 20 to 120 volts with a pulse length of 10 microseconds (μsec) to 100 milliseconds (msec). This electric field induces a dielectric breakdown and pores in the stratum corneum and the vesicles or microbubbles pass through the pores in the SC. Other tissue surfaces will typically require less field strength.

Figure 4:
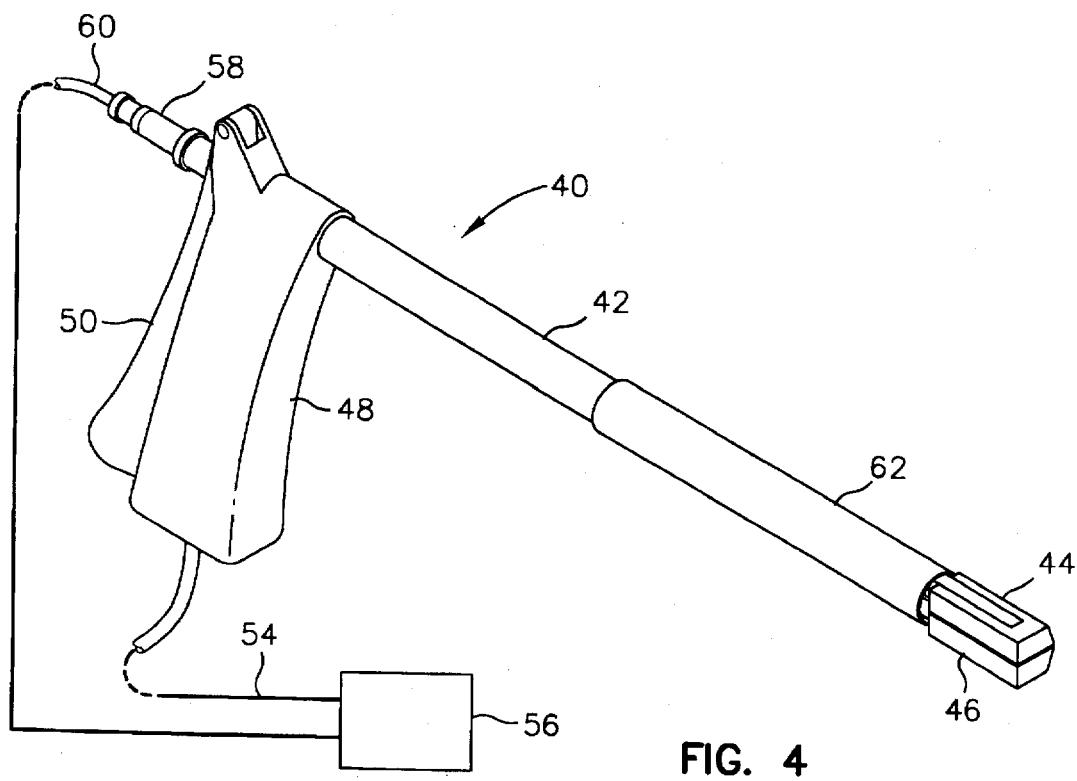
FIG. 4 is a perspective view of a clamp or calipers type electrode apparatus for applying the electric fields and pressure.
Figure 5:
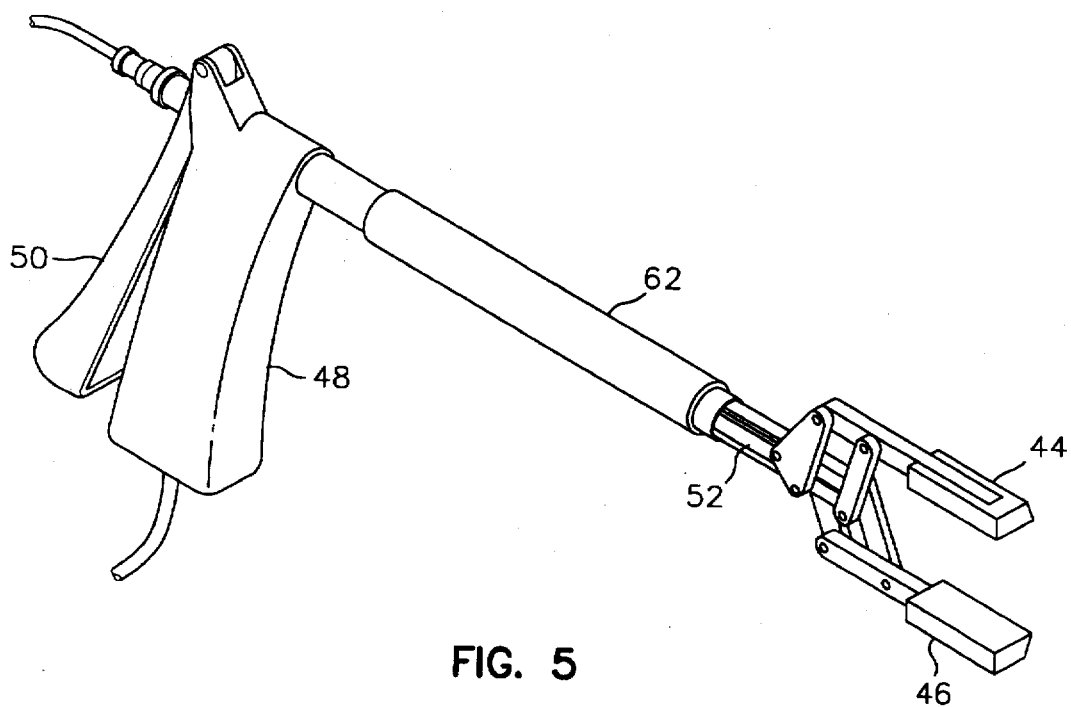
FIG. 5 is a view like FIG. 4. illustrating the calipers in the open position.

Referring to FIG. 4 another type apparatus that may be utilized for carrying out the present invention is illustrated and designated generally by the numeral 40. This device comprises a calipers or forceps device which comprises a support member 42 having a pair of electrodes 44 and 46 mounted on an insulated linkage of the distal end thereof. A pistol grip handle 48 is mounted on a proximal end of the elongated tubular support member for manipulation of same. The electrodes 44 and 46 are mounted on a moveable linkage so that the electrodes move toward and away from one another like the jaws of a clamp. A movable handle 50 is pivotally mounted at an upper end to grip 48 and connects through a moveable or actuating link 52 to the electrode links controlling the spacing between them. The electrodes 44 and 46 may be biased by spring means (not shown) acting between grip 48 and handle 50 to the open or outermost position. The electrodes 44 and 46 are connected through conductors in a cable 54 to suitable power or pulse generator 56.

A suitable sensing unit 58 senses the distance between the electrodes and generates a signal which is transmitted via conductor cable 60 to the pulse generator. The sensing unit 58 may be a device such as a linear potentiometer that provides a resistance directly proportioned to the distance between electrodes 44 and 46. A telescopic sleeve or sheath 62 covers the linkage mechanism during insertion of the conductors into the body.

The distance between the electrodes 42 and 44 is one parameter that goes into the adjustment of the voltage to obtain the optimum amplitude of the electric field to be applied. This parameter and its measure and implementation may be carried out in many ways. A mechanical indicator coupled to the applicator linkage may provide a readout indicating distance in centimeters or other units which the operator enters manually into the electrical field generating machine. A linear or rotational potentiometer connected to the linkage may provide an electrical signal which provides the readout or fed directly into the pulse generator 56.

The electrode distance may also be monitored by a change in capacitance, attenuation of light or other means which generates some form of signal such as an electric signal representative of distance between the electrodes. The signal can then provide means for activating a read-out, such as a numerical indication in centimeters or the like. The signal may also be amplified and directed to suitable control means which functions to set the voltage of a pulse generator 56 in proportion to the distance represented by the signal. This device was designed for use in laparoscopic techniques. However, it and variations thereof are useful for external applications.

In operation, a unit as above described is selected and a selected tissue to be treated is selected and a solution containing molecules to be delivered is applied to the surface of the tissue. The tissue is then placed and gripped between the electrode jaws so that the electrodes supply a pressure to the solution. A signal proportionate to the distance between the electrodes is generated and either manually or electronically entered into the pulse generator 56 so that it generates a pulse proportional to the desired field and applies it to the electrodes. The pulse generator connected to the electrodes is then operated by a trigger switch at the unit, a foot switch, or a switch on the instrument panel for repeatedly applying pulses to the electrodes for generating electric fields of a predetermined amplitude and duration in the tissue between the electrodes. Pores opened up in the tissue surface allow the solution of molecules to enter the tissue aided by the pressure of the electrodes.

The fields are generated by applying a predetermined electric signal to electrodes 44 and 46 of the device. The parameters of the signal are selected so that the tissue between the electrodes is subjected to short pulses of high intensity electric fields sufficient to cause electroporation of the cells of the tissue between the electrodes. The voltage is adjusted accurately so that the generated field has the desired, optimal amplitude. These fields make the walls of the tissue transiently permeable to permit the molecules to enter the tissue. The permeability results from the temporary formation of pores in the tissue walls which are large enough to permit migration of the molecules through the tissue walls.

The invention can also be carried out by other types of instruments including a catheter type apparatus and methods disclosed in the aforementioned Ser. No. 07/907,322 which is incorporated herein by reference as though fully set forth. This provides a more convenient apparatus for the delivery of drugs and genes across tissue surfaces and membranes such as in body cavities. The driving force in this catheter arrangement can be applied by the pressure of the delivery fluid. Other forms of a delivery system could be utilized, such as a small system strapped to the arm or other body part or momentarily connected, containing a rechargeable battery-powered pulse power supply with a reservoir containing fluid containing the drug or other molecules. The fluid could also contain vesicles in suspension with the drug or molecules encapsulated. The applicator would have the basic components as the device in FIG. 1 such that by pushing one button, a preselected amount of solution of molecules or vesicles is delivered to the skin between the electrodes. The solution is are pressed against the skin for good mechanical contact and to apply a driving force. Activating another button or switch delivers an electrical pulse to the electrodes which delivers the molecules through the stratum corneum.

A special patch can also be applied to the tissue surface. The solution can be contained in the patch which also contains the electrode structure to create the electric field. The electrode structure can be similar to that of FIG. 2 and inside or on a surface of the patch. The electrode structure is connected to two electrodes outside the patch so that a pulse generator can be connected momentarily to these outside electrodes to provide a voltage pulse. The patch is preferably provided with an adhesive border to adhere it to the skin or tissue. It is also preferably provided with a protective cover which can be peeled off before adhering the patch to the skin or tissue. The pressure can be applied mechanically by pressing on the patch with any suitable means for applying a reasonably uniform pressure over the desired area.

If the drug is to be transported into the cells, a second pulse after allowing appropriate diffusion time, is applied to open up pores in the cells. This allows the cells to take up the drug or molecules by electroporation.

A drug delivery time profile can be created by mixing different size vesicles. The flux can then be controlled by the pore size and the number of vesicles delivered. The process of the present invention could also be combined with iontophoresis as an additional driving force. The iontophoresis takes advantage of ion charges to cause a migration of the ions or molecules through existing passages or pores in the tissue. The combination could use electroincorporation to deliver vesicles through the SC and then use iontophoresis to induce migration of the drugs, immunizing agents, or genes further into selected tissue.

Figure 6:
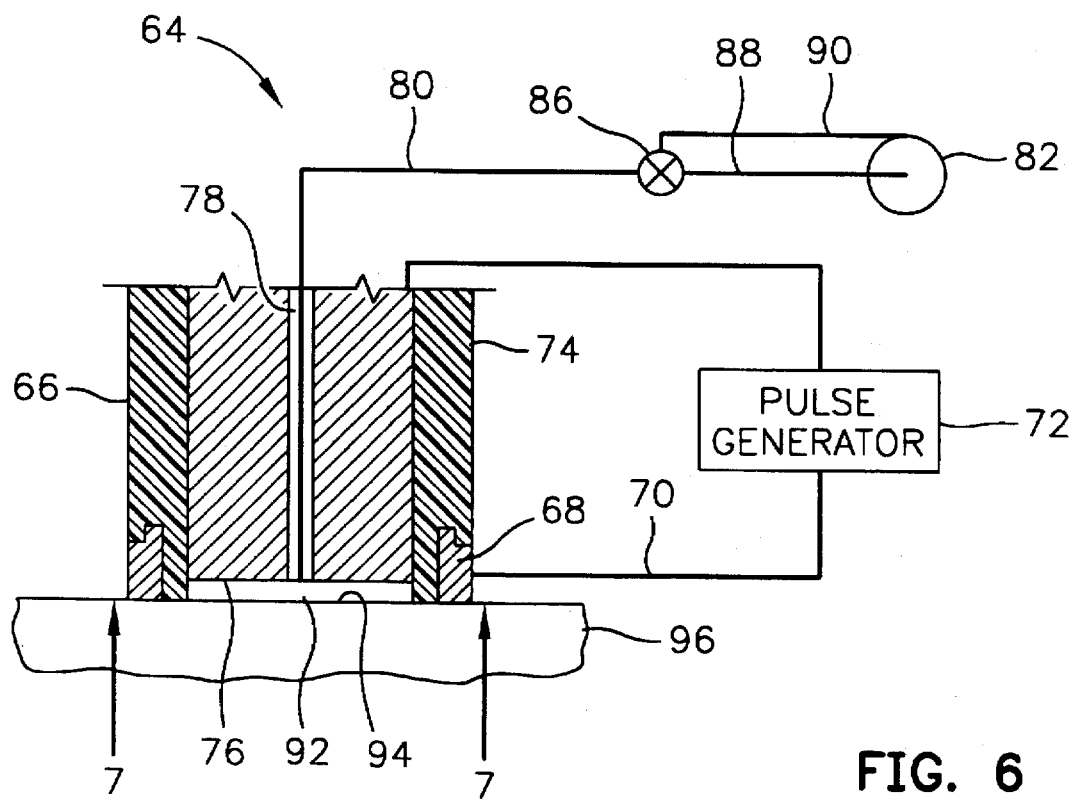
FIG. 6 is a diagrammatic illustration of another apparatus for carrying out the invention.
Figure 7:
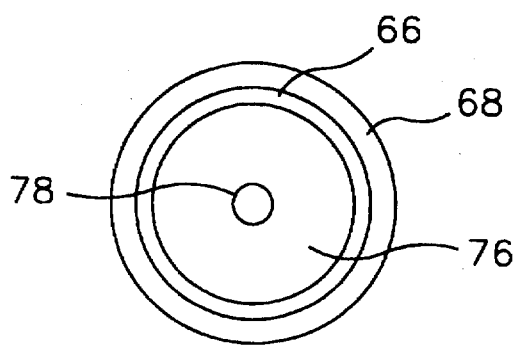
FIG. 7 is a view taken on line 7—7 of FIG. 6.

Referring to FIG. 6, an apparatus for both injecting and withdrawing molecules transdermally is illustrated and designated generally by the numeral 64. The apparatus comprises a suitable housing or holder 66 of suitable insulating material having a tubular configuration. An annular electrode 68 is mounted on an end of the holder and connected by a conductor 70 to a pulse generator 72. An second electrode 74 of a generally tubular configuration is mounted internally of the holder 66 and has an end 76 spaced slightly from the end of the holder. This electrode is connected by a conductor 71 to the pulse generator 72. A central throughbore 78 is connected by a suitable conduit 80 to a pump 82. A valve 86 controls communication of the electrode with either an inlet 88 or an outlet 90 of the pump. The pump can act to supply solution to a chamber 92 formed at an interface of the electrode with a tissue surface or SC 94 of human or animal tissue 96.

When the electrode unit is pressed down against the tissue surface 94, the tissue yields and the electrode surface 76 contacts the surface so that the pulse generator can apply electrical field pulses. This results in electroporation of the surface or SC 94. Simultaneously therewith or within a short time thereafter, the pump may be activated to either supply solution containing the molecules to the SC or a vacuum to withdraw fluid from the tissue. Electroporation of the SC enables the passage of fluid through the SC into or out of the tissue. The electrode face 76 may also be used to apply pressure to a solution of molecules on the surface of the SC to aid in forcing the molecules through the SC.

The present invention has been demonstrated in experiments as follows:

EXPERIMENTAL BACKGROUND:

1. Calcein experiments in vivo in mice

*Solution alone: We demonstrated delivery of Calcein in solution through the skin into the blood with calipers and meander electrodes.

*Solution mixed with empty liposomes: We demonstrated an increased blood uptake of Calcein.

It should be noted that both experiments—solution alone and solution mixed with empty liposomes—gave almost as high a Calcein concentration in the blood as Calcein loaded in liposomes. It is believed that, by increasing the pressure, the concentration will even be substantially higher.

*Solution mixed with gold particles: We demonstrated delivery of Calcein in solution mixed with 1.5–3.0 µm diameter gold particles into the blood. We also observed that a pressure increase leads to higher concentration in the blood.

2. Marker gene experiments in vivo in mice.

We demonstrated the delivery of a naked marker gene lacZ DNA through intact skin and into tissue cells by X-gal staining and observing blue color spots in excised skin cross sections.

Gene expressions were more significant in terms of the number of blue spots if the caliper was held for 10 minutes after the pulse compared to a 1 minute holding time. This substantiates that pores might stay open after the pulse for a period of time during which a pressure mediated delivery of molecules is possible.

Control experiments were performed where the caliper was held on the skin for 11 minutes. Very few blue spots were observed and they appeared to be around hair follicles and in shallower layers of the skin.

3. Theory

1. Poiseuille's law describes the transport of liquids through pores by laminar flow.

Flow through one pore:

i)      $q = (\pi R^4 [p_0 - p_1])/(8\eta L)$    Volume/sec $R$      radius of pore/m $p_0 - p_1$      pressure difference/Newton $\cdot$ m$^{-2}$ $L$      depth of pore/m $\eta$      viscosity of liquid/Newton $\cdot$ sec$^{-1}$ – m$^{-2}$ $q$      flux of liquid/m$^3 \cdot$ sec$^{-1}$ With total number of pores N the total flux Q is:

ii)    $Q = Nq$    m$^3 \cdot$ sec$^{-1}$

From these equations is becomes clear that the pore size plays a major role. If we assume that the total area A occupied by pores ($A \approx N R^2 \pi$) is constant, then it is much more efficient to have fewer but larger pores:

$$Q \approx A R^2 \qquad \text{iii)}$$

This finding confirms that it could be beneficial to mix the solution with large particles to create large pores.

2. Estimate of flux

An estimate of the flux for a typical set of parameters will be derived and compared with an experimentally achieved flux.

$\eta = 6.915 \cdot 10^{-4}$     Newton $\cdot$ sec$^{-1} \cdot$ m$^{-2}$    Viscosity of water $L = 15$ um     Thickness of Stratum Corneum $p_0 - p_1 = 1333$ Newton $\cdot$ m$^{-2}$ Tissue pressure is a few Torr, we assume a pressure difference of 10 Torr, quite a low pressure.

Estimate of pore size and numbers. This is difficult to estimate and influences the calculation strongly. Pliquett/Weaver estimated in their paper that up to 1% of the electroporation area might be covered by pores: "Maximal fractional aqueous area of skin transiently available".

Let's assume a pore size of 8 µm diameter, equal to the size of our large liposomes, and a 1 cm$^2$ area covered by an electrode; this will allow to calculate the number of pores: 2000.

With these numbers, we calculate a flux of 0.013 µl/sec.

If we leave the caliper on for 10 seconds, the amount of liquid transported through the pores is: 0.13 µl.

Comparison with large liposomes/Calcein mixture experiments.

We measured 50 ng/ml×2.5 ml=123 ng in blood. With 25% efficiency of blood uptake, this corresponds to 4×125 ng=0.5 µg of Calcein in the dermis. Started out with 1 µl/µg. Found 0.5 µl in the dermis.

| Experiment: 0.5 ul | Calculation: 0.3 ul |
|---|---|

The difference between experiment and calculation is only a factor 4, which is quite small considering the uncertainty in the number of pores and the applied pressure. If we increase the pressure by a factor 4 to get agreement, this would require a pressure of 40 Torr, which is about 1/20th of an atmosphere. This pressure can be achieved by applying a weight of only 50 g (2 ounces) to an electrode area of 1 cm$^2$.

These estimates indicate that the pressure effect could be a real one and could be used to our advantage. If the positive pressure works, so might a vacuum to draw tissue fluid out e.g. to sense glucose.

We have illustrated and described our invention by means of specific embodiments, it is to be understood that numerous changes and modifications may be made therein without departing from the spirit and scope of the invention as defined in the appended claims.

We claim:

1. A method of transdermal molecular delivery comprising the steps of:
   providing molecules to be delivered through a stratum corneum;
   providing a solution containing particles and said molecules;
   contacting a selected surface area of the stratum corneum with said solution;
   applying a pulsed electric field of sufficient amplitude to induce pores in the stratum corneum; and
   applying a force to said molecules sufficient to induce transport of said molecules through the induced pores in the stratum corneum.

2. A method according to claim 1 wherein the step of applying said electric field includes applying said field with a strength of from about 10 to about 60 kV/cm with a pulse length of from 10 µsec to 100 msec.

3. A method according to claim 2 wherein said force is applied to said molecules within one minute of the electric field.

4. A method according to claim 4 wherein said force is a vacuum.

5. A method according to claim 3 wherein said force is applied by pressurized fluid carrying said molecules.

6. A method according to claim 1 wherein said force is applied by an electrode.

7. A method according to claim 1 wherein said force is applied by the weight of an electrode.

8. A method according to claim 1 wherein said electrical field is applied by a pair of spaced electrodes mounted on a caliper apparatus, and said force is applied by said calipers.

9. A method according to claim 1 wherein said force is applied by an electric field.

10. A method of transdermal molecular delivery comprising the steps of:
    contacting a selected surface area of a stratum corneum with a quantity of molecules to be delivered through the stratum corneum;
    applying a pulsed electric field of sufficient amplitude to induce pores in the stratum corneum; and
    applying a force to said molecules sufficient to induce transport of said molecules through the induced pores in the stratum corneum wherein said force is a vacuum.

11. A method according to claim 10 wherein said electric field is applied by means of a plurality of closely spaced electrodes applied to the stratum corneum and is applied as pulses of from 10 to several hundred volts with a pulse length of between 10 µsec to 100 msec.

12. A method according to claim 11 wherein said molecules are in a solution which includes particles, and said particles are electroincorporated along with said solution.

13. A method according to claim 12 wherein said particles are selected from the group consisting of inert particles, biodegradable particles and particles containing molecules.

14. A method according to claim 12 wherein said inert particles are particles of gold.

15. A method according to claim 12 wherein some of said particles are vesicles containing molecules.

16. A method of transdermal molecular delivery comprising the steps of:
    contacting a selected surface area of the stratum corneum with a quantity of molecules to be delivered through a stratum corneum;
    applying a pulsed electric field of sufficient amplitude to induce pores in the stratum corneum, said electric field is applied by means of a plurality of closely spaced electrodes applied to the surface of the stratum corneum and is applied as pulses of from 10 to several hundred volts with a pulse length of between 10 µsec to 100 msec; and
    applying a force to said molecules sufficient to induce transport of said fluid through the pores in the stratum corneum wherein said pressure is applied by pressurized fluid carrying said molecules.

17. A method according to claim 16 wherein said quantity of molecules includes particles of gold.

18. A method according to claim 16 wherein said quantity of molecules includes particles and some of said particles are vesicles containing molecules.

19. A method of transdermal molecular delivery comprising the steps of:
    incorporating molecules to be delivered in a carrier containing particles;
    contacting a selected area of a stratum corneum with said carrier of the molecules;
    applying a pulsed electric field of sufficient amplitude and duration to induce pores by dielectric breakdown of the stratum corneum;
    and applying a pressure to the molecules to force transport of the molecules through the induced pores in the stratum corneum into underlying tissue.

20. A method according to claim 19 wherein said the step of applying said electric field includes applying said field with a strength of from about 10 to about 60 kV/cm with a pulse length of from 10 µsec to 100 msec.

21. A method according to claim 20 wherein said pressure is applied by pressurized fluid carrying said molecules.

22. A method according to claim 20 wherein said electric field is applied by means of a plurality of closely spaced electrodes applied to the surface of the stratum corneum and is applied as pulses of from 10 to several hundred volts with a pulse length of between 10 μsec to 100 msec.

23. A method according to claim 20 wherein said solution includes inert particles, and said particles are electroincorporated along with said solution.

24. A method according to claim 23 wherein said inert particles are particles of gold.

25. A method according to claim 24 wherein some of said particles are vesicles containing molecules.

26. A method according to claim 19 wherein said step of applying said pressure is carried out by applying pressure by an electrode.

27. A method according to claim 26 wherein said pressure is applied to said carrier within one minute after application of the electric field.

28. A method according to claim 16 wherein said force is applied by an electric field.

* * * * *

UNITED STATES PATENT AND TRADEMARK OFFICE
CERTIFICATE OF CORRECTION

PATENT NO. : 5,688,233
DATED : Nov. 18, 1997
INVENTOR(S) : Hofmann et al.

It is certified that error appears in the above-indentified patent and that said Letters Patent is hereby corrected as shown below:

Column 9, line 52, (Claim 4) change "according to claim 4" to

--according to claim 3--.

Signed and Sealed this

Twentieth Day of January, 1998

Attest:

BRUCE LEHMAN

Attesting Officer     Commissioner of Patents and Trademarks